(12) United States Patent
Braun et al.

(10) Patent No.: US 6,583,313 B1
(45) Date of Patent: *Jun. 24, 2003

(54) TWO PHASE PREPARATION OF CARBOXYLIC ACID ESTERS

(75) Inventors: Max Braun, Wedemark (DE); Kerstin Eichholz, Hannover (DE); Werner Rudolph, Hannover (DE)

(73) Assignee: Solvay Fluor und Derivate GmbH, Hannover (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 569 days.

(21) Appl. No.: 09/113,547

(22) Filed: Jul. 10, 1998

(30) Foreign Application Priority Data

Jul. 25, 1997 (DE) .......................................... 197 32 031

(51) Int. Cl.⁷ ............................................... C07C 67/08
(52) U.S. Cl. ...................................... 560/226; 560/227
(58) Field of Search ................................. 560/226, 227

(56) References Cited

U.S. PATENT DOCUMENTS

| 3,335,173 A | | 8/1967 | Anello ........................ 260/487 |
| 4,916,256 A | | 4/1990 | Grego et al. ................. 560/227 |
| 5,405,991 A | | 4/1995 | Feist et al. .................. 560/239 |
| 5,405,995 A | * | 4/1995 | Feist et al. .................. 560/239 |
| 5,532,411 A | * | 7/1996 | Braun et al. ................. 562/861 |

FOREIGN PATENT DOCUMENTS

| DE | 43 13 793 A1 | 11/1994 |
| EP | 0 209 157 A2 | 1/1987 |
| EP | 0 623 582 A2 | 11/1994 |

* cited by examiner

Primary Examiner—Rosalyn Keys
(74) Attorney, Agent, or Firm—Crowell & Moring LLP

(57) ABSTRACT

The methyl and ethyl esters of trifluoroacetic acid or chlorodifluoroacetic acid can be prepared in a technically simple manner from the corresponding acid chlorides and methanol or ethanol, respectively, in the presence of an "onium" salt of the acid as a catalyst. The alcohol is used in a stoichiometric excess, namely the molar ratio of alcohol to acid chloride is selected such that operation is in the region of a two-phase reaction. One of the phases is formed by the desired ester product, which is obtained in a high purity without any distillation.

8 Claims, No Drawings

TWO PHASE PREPARATION OF CARBOXYLIC ACID ESTERS

BACKGROUND OF THE INVENTION

The invention relates to a method for the catalyzed reparation of methyl and ethyl esters of trifluoroacetic and chlorodifluoroacetic acid.

The methyl and/or ethyl esters of trifluoroacetic and/or chlorodifluoroacetic acid may be used as solvents or cleaning agents. For example, ethyl trifluoroacetate is a solvent in the chlorination of paraffin. The esters are also intermediate products in chemical synthesis. Methyl trifluoroacetate and 1,1,1-trifluoroethyl trifluoroacetate yield trifluoroethanol (and possibly methanol) after hydrogenation. Trifluoroethanol is a solvent and also an intermediate product for the preparation of isofluorane, an anaesthetic. The methyl and ethyl esters of chlorodifluoroacetic acid are likewise synthetic building blocks, for example for the production of liquid crystals.

U.S. Pat. No. 5,405,991 (=EP-A-0,623,582) discloses the preparation of esters of trifluoroacetic acid and of chlorodifluoroacetic acid from the acid chlorides and the corresponding alcohol in the presence of alkali metal or "onium" salts of the carboxylic acid corresponding to the carboxylic acid chloride used.

SUMMARY OF THE INVENTION

It is the object of the present invention to obtain substantially pure esters (degree of purity >94% by weight) in an even simpler manner.

This and other objects have been achieved in accordance with the present invention by providing a method for preparing a methyl or ethyl ester of trifluoroacetic acid or chlorodifluoroacetic acid, comprising reacting an acid chloride of trifluoroacetic acid or chlorodifluoroacetic acid with a stoichiometric excess of methyl or ethyl alcohol in the presence of an onium salt of the acid as a catalyst, the molar ratio of alcohol to acid chloride being selected such that two phases are formed, one phase being an ester phase which without a distillation step contains the ester in a purity of at least 95% by weight.

The invention is based on the observation that in the preparation of the methyl or ethyl esters of trifluoro-acetic acid or of chlorodifluoroacetic acid from the acid chlorides and the alcohol in the presence of "onium" salts of the relevant acids as catalyst, at certain molar ratios two phases form, namely such that in the two-phase region one phase always comprises the substantially pure ester.

DETAILED DESCRIPTION OF PREFERRED EMBODIMENTS

The method according to the invention for the preparation of methyl or ethyl esters of trifluoroacetic acid and of chlorodifluoroacetic acid provides for the acid chloride to be reacted with an excess of the alcohol in the presence of an onium salt of the acid in question and for the molar ratio of alcohol to acid chloride to be selected such that two phases are formed, one phase containing the ester in a purity, achievable without a distillation stage, of at least 95% by weight. The ester can be isolated by separating the ester phase from the other phase. Using this procedure, the ester is thus produced in a purity which makes distillation unnecessary. One preferred embodiment of the method according to the invention therefore provides for the isolation of the resulting ester without distillation. The molar ratio of alcohol to acid chloride is advantageously in the range from 1.01:1 to 5:1.

When preparing the methyl ester of trifluoroacetic acid, the molar ratio of methanol to trifluoroacetyl chloride is in the range from 1.03:1 to 4:1. When preparing the ethyl ester of trifluoroacetic acid, the molar ratio of ethanol to trifluoroacetyl chloride is in the range from 1.01:1 to 5:1. When preparing the methyl ester of chlorodifluoroacetic acid, the molar ratio of methanol to chlorodifluoroacetyl chloride is in the range from 1.06:1 to 2.5:1. When preparing the ethyl ester of chlorodifluoroacetic acid, the molar ratio of ethanol to chlorodifluoroacetyl chloride is in the range from 1.02:1 to 2.5:1. In the above ranges, there are two phases in which, as stated, one phase comprises the ester, which is always contained in a purity of at least 95% by weight. The methyl esters always form the lower phase; the ethyl ester of chlorodifluoroacetic acid likewise forms the lower phase, and the ethyl ester of trifluoroacetic acid forms the upper phase.

As in the generic method, addition of an acid is not necessary, and is preferably not effected. Preferably the method is performed continuously.

As used herein, the term "onium" refers to cations having positively charged nitrogen, for example protonated aromatic nitrogen bases such as pyridinium or protonated alkyl-, dialkyl- or trialkylammonium cations having up to 20 carbon atoms, or for ammonium compounds substituted by cycloalkyl, or cycloaliphatic nitrogen bases such as piperidinium, or quaternary ammonium cations.

Highly suitable carboxylic acid salts. are "onium"salts, "onium" standing for a cation of nitrogen of the formula R'R''R'''R''''N$^+$, in which R', R'', R''' and R''''. independently of each other, stand for hydrogen, alkyl with 1 to 20 carbon atoms, aryl or aralkyl, or wherein R' and R'' or wherein R''' and R'''', or wherein R', R'' and R''', or wherein R', R'', R''' and R'''', optionally with inclusion of the nitrogen atom, form saturated or unsaturated ring systems. "Aryl" here means in particular phenyl, or phenyl substituted by one or more C1–C2-alkyl groups. Salts in which "onium" stands for ammonium, pyridinium or R$^{1'}$R$^{2'}$R$^{3'}$R$^{4'}$N$^+$, in which R$^{1'}$, R$^{2'}$, R$^{3'}$ and R$^{4'}$, independently of each other, are hydrogen, alkyl with 1 to 15 carbon atoms, phenyl or benzyl, are especially suitable. Examples of such cations include pyridinium, piperidinium, anilinium, benzyltriethylammonium and triethylammonium.

The temperature at which the reaction is performed is best from ambient temperature (about 20° C.) up to the boiling point of the mixture, for example up to 100° C. Operation is at ambient pressure (approximately 1 bar absolute) or if desired also at elevated pressure, for example at a pressure of up to 5 bar absolute.

The "onium" salt may be present in catalytic or molar quantities. Advantageously, the molar ratio of the acid halide to the carboxylic acid salt (onium salt) lies within the range from 1:1 to 20:1, but it is possible also to operate outside this range. Surprisingly, the presence of the onium salt results in a greater purity of the ester phase. The optimum quantity of onium salt for achieving a desired purity can be readily determined by orienting tests, simply by analyzing the ester phase in each case, e.g. by a gas chromatogram.

According to one particular embodiment of the invention, the acid chloride and the "onium" salt of the carboxylic acid are produced in situ. To this end, the corresponding "onium" chloride is reacted with the anhydride of the carboxylic acid to be used. During this reaction, the corresponding acid halide and the corresponding salt are formed from the anhydride of the carboxylic acid. With this embodiment, spent halide catalysts can be used as alkali metal or "onium" halide, and in this manner can be converted into valuable products. Preferably pyridinium salts are used.

The invention has the advantage that it is possible to produce carboxylic acid esters without hydrolytic working-up in a technically particularly simple, energy-saving manner.

The invention will be explained in greater detail with reference to the following examples, without being restricted in its scope.

Preparation of Trifluoroacetic Acid Alkyl Esters

EXAMPLE 1

Ethyl Trifluoroacetate.

Formulation

| | |
|---|---|
| 0.3 mole pyridine | 23.7 g |
| 0.3 mole trifluoroacetic acid (TFA) | 34.2 g |
| 3.0 mole ethanol AR | 138.3 g |
| 2.7 mole trifluoroacetyl chloride (TFAC) | 357.7 g |

Procedure

The pyridine was placed in a 500 ml three-necked flask with a magnetic stirrer rod, temperature sensor and a dry ice cooler, and TFA was added dropwise. The reaction was exothermic. Before the pyridinium trifluoroacetate crystallized, the ethanol was added in order to keep it in solution. The temperature of the reaction mixture was pre-controlled to 50° C. in an oil bath and at this temperature the TFAC was introduced via a glass frit. At 20% of the quantity of TFAC stoichiometric to the ethanol, two phases were formed, the upper phase being virtually pure ethyl trifluoroacetate. Once the introduction of TFAC had ended (2.7 moles, 90% of the stoichiometric quantity), the reaction mixture was transferred into a separating funnel. Both phases were clear, and the catalyst phase was slightly yellow in color. Analysis of the ester phase was effected using gas chromatography, and yielded ester of 97% purity. The ester yield isolated in this test was 96.6% of theoretical. Sampling from the ester phase in the two-phase region at 50, 60, 70, 80 and 90% of the stoichiometric amount of TFAC yielded comparable ester purities in each case. The two-phase region ester phase/catalyst phase was not left until 99% of the TFAC/alcohol stoichiometry.

EXAMPLE 2

Methyl Trifluoroacetate

Formulation

| | |
|---|---|
| 0.3 mole pyridine | 23.7 g |
| 0.3 mole trifluoroacetic acid (TFA) | 34.2 g |
| 3.0 mole methanol | 96.12 g |
| 2.7 mole trifluoroacetyl chloride (TFAC) | 357.70 g |

Procedure

The pyridine was placed in a 500 ml three-necked flask with a magnetic stirrer rod, temperature sensor and a dry ice cooler, and TFA was added dropwise. The reaction was exothermic. Before the pyridinium trifluoroacetate crystallized, the methanol was added in order to keep it in solution. The temperature of the reaction mixture was pre-controlled to 50° C. in an oil bath and at this temperature the TFAC was introduced via a glass frit.

At 25% of the TFAC required, two phases were formed, the lower phase being virtually pure methyl trifluoroacetate. The temperature dropped during the reaction to the boiling temperature of the ester. The reaction lasted 3 hours. Analysis of the ester phase was effected using gas chromatography and yielded 98.5% ester. The isolated ester yield was 95.2% of theoretical. Sampling from the ester phase in the two-phase region at 50, 60, 70, 80 and 90% of the stoichiometric amount of TFAC yielded comparable ester purities in each case. The two-phase region ester phase/catalyst phase was not left until 97% of the TFAC/alcohol stoichiometry.

Preparation of Chlorodifluoroacetic Acid alkyl Esters

EXAMPLE 3

Methyl Chlorodifluoroacetate

Formulation

| | |
|---|---|
| 0.2 mole pyridine | 23.7 g |
| 0.19 mole chlorodifluoroacetic acid (CDFA) | 34.2 g |
| 2.0 mole methanol AR | 138.3 g |
| 1.8 mole chlorodifluoroacetyl chloride (CDFAC) | 268.06 g |

Procedure

The pyridine was placed in a 500 ml three-necked flask with a magnetic stirrer rod, temperature sensor and a dry ice cooler, and CDFA was added dropwise. The reaction was exothermic. Before the pyridinium chlorodifluoroacetate crystallized, the methanol was added in order to keep it in solution. The temperature of the reaction mixture was pre-controlled to 50° C. in an oil bath, and at this temperature the CDFAC was introduced via the dropping funnel.

At approximately 40% of the quantity of CDFAC stoichiometric to the alcohol, two phases were formed, the lower phase being virtually pure methyl chlorodifluoroacetate. Once the dropwise introduction of 1.8 mole CDFAC had ended, subsequent stirring was briefly carried out, and then the phases were separated. The phases were clear after separation, and the catalyst phase was dark yellow in color. The ester phase was investigated using gas chromatography and yielded a methyl chlorodifluoroacetate purity of 95%. The two-phase region ester phase/catalyst phase was not left until 94% of the CDFAC/alcohol stoichiometry.

EXAMPLE 4

Ethyl Chlorodifluoroacetate

Formulation

| | |
|---|---|
| 0.2 mole pyridine | 23.7 g |
| 0.19 mole chlorodifluoroacetic acid (CDFA) | 34.2 g |
| 2.0 mole ethanol AR | 92.12 g |
| 1.8 mole chlorodifluoroacetyl chloride (CDFAC) | 268.06 g |

Structure and Procedure

The pyridine was placed in a 500 ml three-necked flask with a magnetic stirrer rod, temperature sensor and a dry ice cooler, and CDFA was added dropwise. The reaction was exothermic. Before the pyridinium chlorodifluoroacetate crystallized, the ethanol was added in order to keep it in solution. The temperature of the reaction mixture was pre-controlled to 50° C. in an oil bath, and at this temperature CDFAC was introduced dropwise via a dropping funnel.

At approximately 40% of the quantity of CDFAC stoichiometric to the alcohol, two phases were formed, the lower phase being virtually pure ethyl chlorodifluoroacetate. Once the dropwise introduction of 1.8 mole CDFAC had ended, subsequent stirring was briefly carried out, and then the phases were separated.

The phases were clear after separation, and the catalyst phase was dark yellow in color. Analysis of the ester phase yielded an ester purity of 96.5%. The two-phase region was not left until 98% of the CDFAC/alcohol stoichiometry.

Once the ester phase had been separated, the onium salt was able to be used again several times as a catalyst for the esterification reaction according to the invention. Thus the method can also be performed continuously.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A method for preparing a methyl or ethyl ester of trifluoroacetic acid or chlorodifluoroacetic acid, comprising:

reacting an acid chloride of trifluoroacetic acid or chlorodifluoroacetic acid with a stoichiometric excess of methyl or ethalcohol in the presence of an onium salt of the acid as catalyst, wherein the molar ratio of alcohol to acid chloride is selected such that two phases can form;

allowing an upper phase and a lower phase to form, one phase being an ester phase which contains the ester in a purity, achievable without a distillation stage, of at least 95% by weight; and separating said ester phase.

2. A method according to claim 1, wherein the molar ratio of alcohol to acid chloride is in the range from 1.01:1 to 5:1.

3. A method according to claim 1, wherein the method is carried out continuously.

4. A method according to claim 1, wherein the methyl ester of trifluoroacetic acid is prepared, and the molar ratio of methanol to trifluoroacetyl chloride is in the range from 1.03:1 to 4:1.

5. A method according to claim 1, wherein the ethyl ester of trifluoroacetic acid is prepared, and the molar ratio of ethanol to trifluoroacetyl chloride is in the range from 1.01:1 to 5:1.

6. A method according to claim 1, wherein the methyl ester of chlorodifluoroacetic acid is prepared, and the molar ratio of methanol to chlorodifluoroacetyl chloride is in the range from 1.06:1 to 2.5:1.

7. A method according to claim 1, wherein the ethyl ester of chlorodifluoroacetic acid is prepared, and the molar ratio of ethanol to chlorodifluoroacetyl chloride is in the range from:1.02:1 to 2.5:1.

8. A method according to claim 1, wherein said onium salt used as a catalyst is a pyridinium salt of the respective acid.

* * * * *